(12) United States Patent
Lee et al.

(10) Patent No.: US 11,493,219 B2
(45) Date of Patent: Nov. 8, 2022

(54) INTELLIGENT AIR SHIELD FORMATION DEVICE FOR PREVENTING INFECTION

(71) Applicant: Sangyul Lee, Seoul (KR)

(72) Inventors: Keun Seok Lee, Seoul (KR); Sangyul Lee, Seoul (KR)

(73) Assignee: Sangyul Lee, Seoul (KR)

( * ) Notice: Subject to any disclaimer, the term of this patent is extended or adjusted under 35 U.S.C. 154(b) by 0 days.

(21) Appl. No.: 17/535,673

(22) Filed: Nov. 25, 2021

(65) Prior Publication Data

US 2022/0249728 A1    Aug. 11, 2022

(30) Foreign Application Priority Data

Feb. 8, 2021    (KR) .................... 10-2021-0017758

(51) Int. Cl.
| | |
|---|---|
| F24F 11/00 | (2018.01) |
| F24F 9/00 | (2006.01) |
| F24F 11/79 | (2018.01) |
| G06V 40/10 | (2022.01) |
| F24F 8/22 | (2021.01) |

(52) U.S. Cl.
CPC ............ *F24F 11/0001* (2013.01); *F24F 9/00* (2013.01); *F24F 11/79* (2018.01); *G06V 40/10* (2022.01); *F24F 8/22* (2021.01); *F24F 2009/007* (2013.01)

(58) Field of Classification Search
CPC .......... F24F 9/00; F24F 2009/007; F24F 3/16; F24F 2120/12; G06V 40/10; A61L 9/20; A61L 2209/111; A61L 2209/12

USPC ......................................................... 454/188
See application file for complete search history.

(56) References Cited

U.S. PATENT DOCUMENTS

| | | | | |
|---|---|---|---|---|
| 10,571,144 | B2 * | 2/2020 | Kanada .................. | G08C 23/04 |
| 2005/0136827 | A1 * | 6/2005 | Basset ..................... | F24F 9/00 |
| | | | | 454/187 |
| 2014/0309752 | A1 * | 10/2014 | Yuzurihara ........... | H05B 47/115 |
| | | | | 700/13 |
| 2014/0342649 | A1 * | 11/2014 | Boni ....................... | F24F 9/00 |
| | | | | 454/78 |
| 2015/0005951 | A1 * | 1/2015 | Srinivasan ............ | G05B 15/02 |
| | | | | 700/275 |
| 2016/0131391 | A1 * | 5/2016 | He ......................... | F24F 11/79 |
| | | | | 454/292 |
| 2018/0335228 | A1 * | 11/2018 | Brown .................... | F24F 6/12 |
| 2019/0174915 | A1 * | 6/2019 | Prince .................... | F24F 9/00 |
| 2019/0309978 | A1 * | 10/2019 | Song ..................... | F24F 11/58 |

(Continued)

FOREIGN PATENT DOCUMENTS

| | | | | |
|---|---|---|---|---|
| CN | 109059205 A | * | 12/2018 | ............ F24F 11/63 |
| CN | 110081531 A | * | 8/2019 | |

(Continued)

*Primary Examiner* — Edelmira Bosques
*Assistant Examiner* — Frances F. Hamilton
(74) *Attorney, Agent, or Firm* — Nicholas Park

(57) ABSTRACT

The present invention provides an intelligent air shield formation device, having a plurality of nozzles are configured to discharge purified air towards ground, detecting a body region of the detected person, generating region information, controlling the plurality of nozzles corresponding to the region information, generating movement information based on a speed of movement of the body region, controlling the shape of the region information to be deformed based on the movement information.

16 Claims, 9 Drawing Sheets

(56) References Cited

U.S. PATENT DOCUMENTS

| | | | |
|---|---|---|---|
| 2021/0003301 A1* | 1/2021 | Takayanagi | F24F 11/79 |
| 2021/0381713 A1* | 12/2021 | Kim | F24F 8/20 |
| 2022/0034526 A1* | 2/2022 | Sims, Jr. | F24F 9/00 |
| 2022/0034542 A1* | 2/2022 | Peters | F24F 3/16 |
| 2022/0057094 A1* | 2/2022 | Chinnappa Reddy | B60H 1/00371 |
| 2022/0163223 A1* | 5/2022 | Suetsugu | F24F 7/06 |
| 2022/0252295 A1* | 8/2022 | Liu | F24F 7/003 |

FOREIGN PATENT DOCUMENTS

| | | | | |
|---|---|---|---|---|
| CN | 110645686 A | * | 1/2020 | F24F 11/64 |
| CN | 112325419 A | * | 2/2021 | E01F 13/04 |
| CN | 110360715 B | * | 9/2021 | F24F 11/30 |
| CN | 112032920 B | * | 1/2022 | F24F 11/32 |
| JP | 2010286165 A | * | 12/2010 | |
| JP | 2011-257011 A | | 12/2011 | |
| JP | 2011257011 A | * | 12/2011 | |
| JP | 6624706 B1 | * | 12/2019 | |
| KR | 101916190 B1 | * | 9/2017 | |
| KR | 10-1916190 B1 | | 11/2018 | |
| KR | 102177840 B1 | * | 2/2020 | |
| KR | 102263908 B1 | * | 6/2020 | F24F 11/30 |
| KR | 102337250 B1 | * | 6/2020 | |
| KR | 102263908 B1 | * | 7/2020 | |
| KR | 102264493 B1 | * | 10/2020 | |
| KR | 102337250 B1 | * | 12/2021 | F24F 11/30 |
| WO | WO-2016067719 A1 | * | 5/2016 | |
| WO | WO-2016157568 A1 | * | 10/2016 | F24F 11/52 |

* cited by examiner

INTELLIGENT AIR SHIELD FORMATION DEVICE FOR PREVENTING INFECTION

CROSS-REFERENCE TO RELATED APPLICATION

This application claims priority to and the benefit of Korean Patent Application No. 10-2021-0017758, filed on Feb. 8, 2021, the disclosure of which is incorporated herein by reference in its entirety.

BACKGROUND

1. Field of the Invention

The present invention relates to an intelligent air shield formation device and method capable of preventing infection, and more particularly, to an intelligent air shield formation device and method for generating an air shield to prevent infection among people.

2. Discussion of Related Art

Highly contagious diseases, such as coronavirus (COVID-19), are easily transmitted from person to person through droplets. Accordingly, as a method of preventing infection through droplets, wearing a mask is a representative method.

On the other hand, since most of the indoor space cannot be ventilated naturally, there is a problem of being vulnerable to infection. Moreover, in the case of an indoor space where frequent conversation among people is required, the possibility of infection by droplets generated during conversation is further increased.

In addition, in the case of a store that sells food such as restaurants and cafes, customers have no choice but to remove the mask while eating food, and when there is another customer sitting at one table facing each other, virus through droplets increases the risk of infection. In addition, even if a customer is seated at another table, there is a possibility of infection through the influence of wind by the distance, direction, or fan of the table.

In this regard, conventionally, infection has been prevented by detecting a person entering and leaving an indoor space using a camera and measuring the detected person's body temperature to identify a person with a high body temperature. However, It is merely a basic preventive method to prevent infection of an indoor space.

Accordingly, there is a need for a method for effectively preventing infection among people in an indoor space.

SUMMARY OF THE INVENTION

The technical problem to be solved by the present invention is to provide an intelligent air shield formation device and method capable of preventing infection by generating an air shield around a person so that infection among people can be prevented in a space where the intelligent air shield formation device is installed.

One aspect of the present invention, comprises an intelligent air shield formation device comprising: a main module comprising a plurality of nozzles are configured to discharge purified air towards ground; a detection module is configured to detect a person using the space provided with the main module and detecting a body region of the detected person; and a control module is configured to generate region information of a shape surrounding the body region, is configured to control the plurality of nozzles corresponding to the region information, is configured to generate movement information based on a speed of movement of the body region, and is configured to control the shape of the region information to be deformed based on the movement information, wherein the detection module is configured to generate temperature information by measuring the temperature of the body region, wherein the control module is configured to control the area of the region information to increase as the temperature of the body region increases.

The detection module may configured to detect a noise generated from the body region, and generate a noise information to indicate the size of the noise.

The control module may configured to control the area of the region information to increase as the size of the noise information increases.

The control module may configured to indicate a location that an arbitrary object is installed.

The control module may configured to set an object region including the location that the object is installed.

The control module may configure to recognize an overlapping region where the region information and the location that the object is installed overlaps.

The control module may configure to extend the object region by including the region information to the object region, when the area of the overlapping region is greater than or equal to predetermined area of object.

One aspect of the present invention, comprises a method of forming intelligent air shield by intelligent air shield formation device, wherein the intelligent air shield formation device comprises a main module comprising a plurality of nozzles are configured to discharge purified air towards ground, comprising:

detecting, by a detection module, a person using the space provided with the main module and detecting a body region of the detected person;

generating, by a control module, a region information of a shape surrounding the body region;

controlling, by the control module, the plurality of nozzles corresponding to the region information;

generating, by the control module, movement information based on a speed of movement of the body region;

controlling, by the control module, the shape of the region information to be deformed based on the movement information;

generating, by the detection module, temperature information by measuring the temperature of the body region; and controlling, by the control module, the area of the region information to increase as the temperature of the body region increases.

The detection module may detect a noise generated from the body region, and generating, by the detection module, a noise information to indicate the size of the noise.

The control module may control the area of the region information to increase as the size of the noise information increases.

DETAILED DESCRIPTION OF EXEMPLARY EMBODIMENTS

Figure 1:
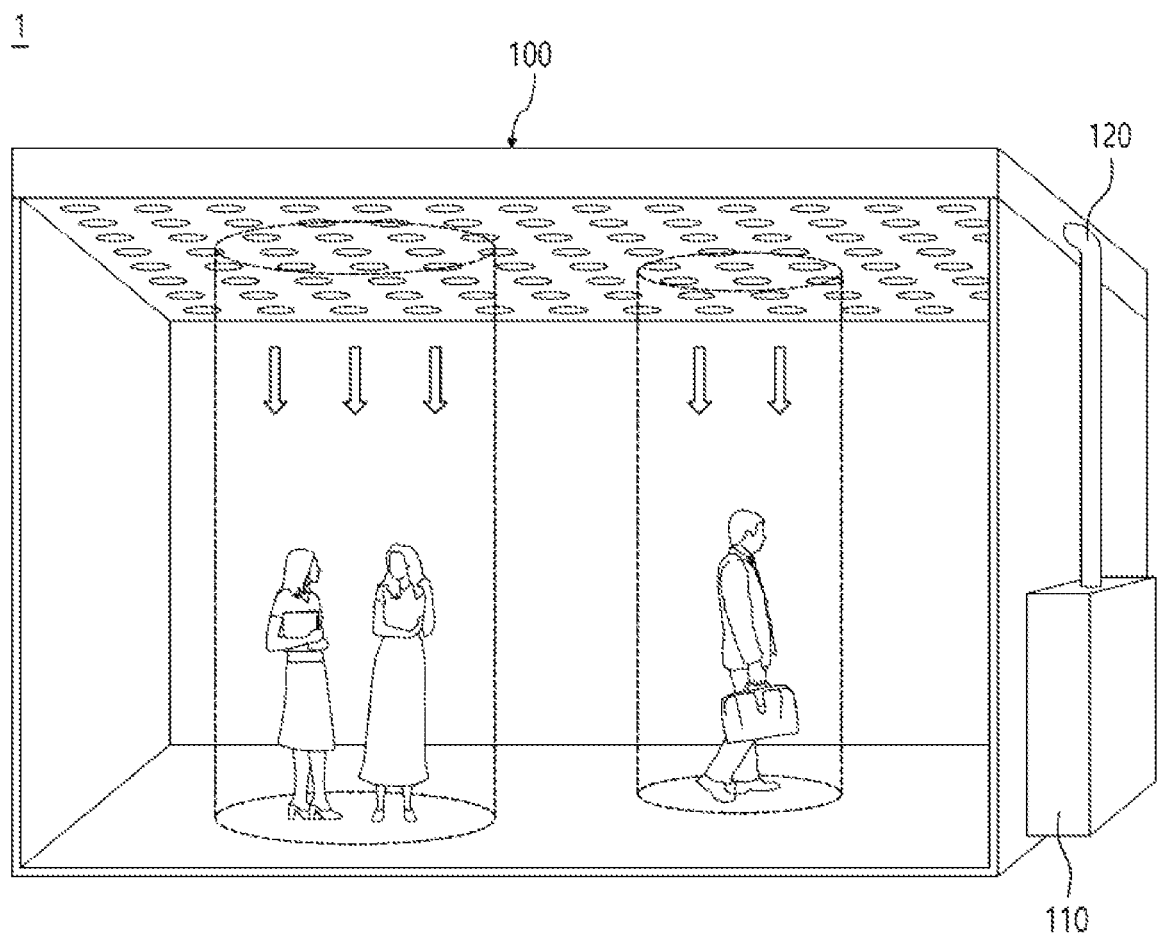
FIG. 1 is a schematic diagram of an intelligent air shield formation device according to an embodiment of the present invention.

Reference is made to the accompanying drawings, which show by way of illustration specific embodiments in which the present invention may be practiced. These embodiments are described in sufficient detail to enable those skilled in the art to practice the present invention. It should be understood that the various embodiments of the present invention are different but need not be mutually exclusive. For example, certain shapes, structures, and characteristics described herein may be implemented in other embodiments without departing from the idea and scope of the invention with respect to one embodiment. In addition, it should be understood that the location or arrangement of individual components within each disclosed embodiment may be changed without departing from the idea and scope of the present invention. Accordingly, the following detailed description is not intended to limit the scope of the present invention, if properly described, is limited only by the appended claims, along with all scope equivalents to those claimed. Like reference numerals in the drawings refer to the same or similar functions throughout the various aspects.

Hereinafter, preferred embodiments of the present invention will be described in more detail with reference to the drawings.

FIG. 1 is a schematic diagram of an intelligent air shield formation device according to an embodiment of the present invention.

The intelligent air shield formation device 1 can be provided to prevent infection among people using the space where the intelligent air shield formation device 1 is installed.

Here, the intelligent air shield formation device 1 forms an air curtain or air shield around the person using the space where the intelligent air shield formation device 1 is installed.

Accordingly, the intelligent air shield formation device 1 can prevent the exchange of droplets among people. In addition, the intelligent air shield formation device 1 may directly or indirectly prevent physical contact among people. Through this, the intelligent air shield formation device 1 can prevent infection among people.

As such, the intelligent air shield formation device 1 may comprise a main module 100, a detection module 200 and a control module 300.

In addition, the intelligent air shield formation device 1 may be implemented by more components than the components as shown in FIG. 1 and may be implemented by fewer components. Alternatively, the intelligent air shield formation device 1 is at least two components provided in the intelligent air shield formation device 1 are integrated into a single component, and the single component may perform a complex function. Hereinafter, the above-described components will be described in detail.

The main module 100 may be provided with a plurality of nozzles 130 for discharging purified air toward the ground.

In more detail, the main module 100 may comprise a purifier 110, a transporter 120, a nozzle 130, and a light-emitter 140.

The purifier 110 may induce air. The purifier 110 may purify the introduced air. For this reason, the purifier 110 may comprise one or more fans. Through this, the purifier 110 may rotate the fan to induce air to be introduced into the purifier 110.

On the other hand, the purifier 110 may be provided with a purification filter, a sterilizer lamp, a plasma generator, etc. to purify the introduced air to generate purified air.

Here, the purification filter may comprise a plurality of single filters of different shapes. Each of these single filters can collect or filter out different contaminants.

For example, a single filter is a pre-filter for collecting dust with large particles contained in the air), an active carbon filter for collecting particles such as odors, harmful gases or TVOC (Total Volatile Organic Compounds) contained in air, and It may comprise a H13 HEPA filter (High Efficiency Particulate Air Filter) for collecting particles such as ultra-fine dust of 2.5 micrometers or less contained in the air. In this case, the purification filter may have the shape of a triple-layered filter including a free filter, an active carbon filter, and an H13 HEPA filter.

As such, a single filter has a mesh shape, allowing air to pass through and to filter out contaminants. In this case, the single filter may be made of a metal material or a synthetic resin material.

In addition, the purification filter may utilize a plurality of different filters previously known.

The sterilizer lamp can sterilize the air exhausted from the cross-flow fan by emitting ultraviolet light.

Here, the sterilizer lamp may emit ultraviolet light having a wavelength in the range of 100 nanometers to 280 nanometers. For example, the sterilizer lamp may be a UV-C ultraviolet sterilizer lamp.

The plasma generator can absorb the bacteria present in the air by applying a voltage to the air discharged from the cross-flow fan.

In this case, the plasma generator may be provided with an ionizer and a flat electrode. In this case, the ionizer may apply a high voltage to the electrode to cause the bacteria or the like present in the air to be charged. A high voltage is applied to the flat electrode, so that bacteria, etc. that are charged by the ionizer can be adsorbed.

As such, the purifier 110 may generate purified air by passing the air through at least one of a purification filter, a sterilizer lamp, and a plasma generator.

The transporter 120 may transport purified air generated by the purifier 110.

In this case, the transporter 120 may have a hose shape connecting the purifier 110 and the nozzle 130. The transporter 120 may comprise one or more fans so that purified air supplied from the purifier 110 can be moved to the nozzle 130.

In addition, the transporter 120 may comprise one or more fans to allow purified air to be discharged to the outside of the nozzle 130 to form an air shield.

The nozzle 130 can control the direction in which purified air is discharged.

For this reason, the nozzle 130 may be opened or closed according to a control signal transmitted from the control module 300. Here, the opening of the nozzle 130 may mean a state in which purified air is discharged from the nozzle 130. When the nozzle 130 is closed, it may mean a state in which purified air is not discharged from the nozzle 130.

In addition, the nozzle 130 may control the direction in which purified air is discharged from the nozzle 130 according to a control signal transmitted from the control module 300.

Here, the direction in which purified air is discharged may mean an angle at which purified air is discharged relative to the ground. For example, the nozzle 130 may be oriented so that purified air is discharged perpendicular to the ground. In addition, the nozzle 130 can be directed so that purified air is discharged at a constant angle with respect to the ground.

On the other hand, the nozzle 130 may be installed in a preset arrangement of a plurality of nozzles (130). Through this, the main module 100 may form an air shield around the person.

Here, the plurality of nozzles 130 may be installed to be arranged along the vertical axis and the horizontal axis. Through this, the plurality of nozzles 130 may be installed to indicate their respective positions based on the arrangement.

The light-emitter 140 may be disposed on one side of the nozzle 130. The light-emitter 140 may emit light by the control module 300. In this case, the light-emitter 140 may be composed of an LED element or the like.

The detection module 200 may detect a person using the space from which the main module 100 is discharged. The detection module 200 may detect a detected human body region.

For this reason, the detection module 200 may transmit signals such as ultraviolet rays and infrared rays. The detection module 200 may comprise a sensor that detects a person by receiving a reflected signal. In this case, a plurality of detection modules 200 may be disposed on one side of the nozzle 130.

Accordingly, the detection module 200 may detect a person according to a change in the reflected signal. The detection module 200 may detect a body region according to a sensor detected by a person.

Meanwhile, the detection module 200 may be provided with a camera that generates image information. In this case, the detection module 200 may be installed on one side of the space where the intelligent air shield formation device 1 is installed.

Here, the detection module 200 is provided with a plurality of cameras, it may be provided to divide the space in which the intelligent air shield formation device 1 is installed through a plurality of cameras. Accordingly, the detection module 200 may detect a person from image information, and a person detection model may be prepared to detect a body region.

In this regard, the human detection model may be learned using an artificial intelligence (AI) technique such as machine learning. Here, machine learning may be understood as a technique of generating a learning model to classify a plurality of information into one or more groups based on a plurality of pieces of information, and classifying arbitrary information based on the generated learning model. Such machine learning may comprise supervised learning for generating a learning model to classify arbitrary information according to a plurality of pieces of information classified by an administrator. Machine learning may comprise unsupervised learning in which a plurality of pieces of information are analyzed or a clustering process is performed to generate a learning model. Machine learning can include semi-supervised learning that creates a learning model by mixing supervised and unsupervised learning. Machine learning may include reinforcement learning that generates a learning model according to a reward generated in the process of performing an arbitrary operation on a plurality of pieces of information.

Accordingly, the detection module 200 may learn a human detection model by receiving a human body region from a plurality of pre-prepared image information.

Meanwhile, the detection module 200 may detect a person and detect a body region using a thermal camera or the like.

Also, the detection module 200 may measure the temperature of the body region to generate temperature information. For this reason, the detection module 200 may use a thermal camera or a thermal sensor.

The detection module 200 may detect noise generated from the body region side. The detection module 200 may generate noise information to indicate the level of noise.

For this reason, the detection module 200 may be provided with a plurality of microphones. In this case, the plurality of microphones may be disposed on one side of the main module 100, and the level of noise generated from the body region may be sensed according to noise information generated from the microphone closest to the position where the body region is detected.

The control module 300 may generate region information having a shape that surrounds the body region. The control module 300 may control the plurality of nozzles 130 corresponding to region information to discharge purified air.

Also, the control module 300 may generate movement information based on the speed at which the body region moves. The control module 300 may control the shape of the region information to be deformed based on the movement information.

Here, the region information may be provided in a shape that surrounds the body region. For example, the region information may be provided in a circular shape surrounding the body region.

In this case, the control module 300 may generate region information in a circular shape centered on the central point of the body region. In this case, the control module 300 may detect an outer point of the body region that is farthest from the center point of the body region. Accordingly, the control module 300 may generate region information such that a preset distance interval is separated from the detected outer point.

Accordingly, the control module 300 may control the plurality of nozzles 130 to form an air shield by discharging purified air according to region information. Through this, the control module 300 can control the plurality of nozzles 130 so that a person is located inside the air shield formed according to region information.

For this reason, the region information may be provided to comprise the positions of the plurality of nozzles 130 corresponding to the region information.

In addition, when the nozzle 130 is provided in a straight shape, the control module 300 may control the direction of the plurality of nozzles 130 so that the plurality of nozzles 130 form an air shield having a circular shape.

Meanwhile, the movement information may indicate a speed at which the body region moves. Here, the speed at which the body region moves may comprise a direction in which the body region moves and a speed at which the body region moves. In other words, the movement information can be understood as a vector representing the path the body region moves. Accordingly, the movement information may be provided to comprise the position of the body region, the direction in which the body region moves, and the speed at which the body region moves.

Accordingly, the control module 300 may correct region information based on the movement information. Here, correcting the region information may be understood as changing the positions of the plurality of nozzles 130 corresponding to the region information.

Through this, the control module 300 may maintain the air shield formed around the moving person according to the correction of the region information.

Meanwhile, as the speed according to the movement information increases, the control module 300 may control the outer side in the direction according to the movement information in the region information to be farther from the center of the region information.

For example, when the region information is generated in a circular shape, the control module 300 may control the region information to be generated in a more distorted elliptical shape as the speed according to the movement information increases. The control module 300 may control the region information to be generated closer to a circular shape as the speed according to the movement information is slower.

On the other hand, the control module 300 may control the nozzle 130 so that, when different people are adjacent to each other by a predetermined distance or more, the adjacent people are comprised inside one air shield.

For this reason, the control module 300 may extend each region information into one region information embracing a plurality of body regions based on a plurality of movement information, in case that that a plurality of body regions converge to an arbitrary face-to-face, and in case that the distance interval from the outside in the direction according to the movement information in each region information to the face-to-face region is less than or equal to the first distance interval set in advance.

Here, the face-to-face region may be configured to detect intentions that different people face each other. For example, the face-to-face region may indicate a space range in which the body region is expected to move based on movement information. In this case, the face-to-face region may be set to have a circular shape whose diameter is a preset distance interval.

Accordingly, the control module 300 may calculate a future position after a preset time interval from the current position of the body region based on the movement information. When future positions of different body regions exist in the face-to-face region, the control module 300 may determine that the plurality of body regions converge to an arbitrary face-to-face region.

In this case, the control module 300 may calculate a distance interval from the outside of the current region information to the face-to-face region. In addition, when the calculated distance interval is less than or equal to the first distance interval, the control module 300 may extend region information.

Accordingly, the control module 300 may remove the expanded region information while the region information is expanded and regenerate region information for different body regions, in case that the future positions of different body regions existing inside the extended region information are located outside of the face-to-face region.

Meanwhile, the control module 300 may control the area of the region information to increase as the temperature of the body region increases.

In addition, the control module 300 may control the area of the region information to increase as the size of the noise information increases.

Through this, the control module 300 can prevent transmission from a person with a high possibility of infection.

The control module 300 may recognize an overlapping region in which the extended region information and other region information overlap when a part of the extended region information is overlapped with at least part of the other region information according to the level of noise.

The control module 300 may calculate the nozzle angle corresponding to the overlapping region. The control module 300 may control one or more nozzles located in the overlapping region to be inclined to the inside of the other region information according to the calculated nozzle angle.

Here, the nozzle angle may be set so that the angle increases as the overlapping region becomes wider. Accordingly, the control module 300 can minimize the possibility of spreading the droplets of a person with a high possibility of infection.

In addition, the control module 300 may control the area of a region less than a second distance interval from the face-to-face region in the region information to increase, according to the size of the noise information, based on a plurality of movement information, in case that a plurality of body regions converge to an arbitrary face-to-face region, in case that the distance interval from the outside to the face-to-face region according to the movement information in each region information exceeds the first distance interval set in advance and is less than or equal to a second distance interval set in advance.

Through this, the control module 300 can suppress, as much as possible, a droplet that is likely to spread further as the sound of a person's speech increases.

Here, the second distance interval may be set to be larger than the first distance interval.

On the other hand, the control module 300 can control the nozzle 130 so that when a person uses the object installed in the space where the intelligent air shield formation device 1 is installed, the air shield embraces the area where the object is installed.

For this reason, the control module 300 may set an object region to indicate a location where an arbitrary object is installed. The control module 300 may recognize an overlapping region where the object region and region information overlap. The control module 300 may extend region information to an object region when the area of the overlapping region is greater than or equal to a preset area of object.

Here, the object region can be configured to embrace the objects installed in the space where the intelligent air shield formation device 1 is installed. For example, an object region can be configured to embrace a dining table set up for human use.

In addition, the preset area of object may be set to determine whether a person uses the object. For example, the area of object may be set to indicate a case where the overlapping region is ½ of the region information.

In this way, the area of object may be set to indicate the ratio of the overlapping region to the region information.

Meanwhile, the control module 300 may control the light-emitter 140 to light when the nozzle 130 is opened. And, when the nozzle 130 is closed, the control module 300 may control the light-emitter 140 to turn off.

In this case, the control module 300 may control the light-emitter 140 to be turned on along the air shield.

Also, when region information is expanded, the control module 300 may control the light-emitter 140 corresponding to the expanded region to be turned on.

Figure 2:
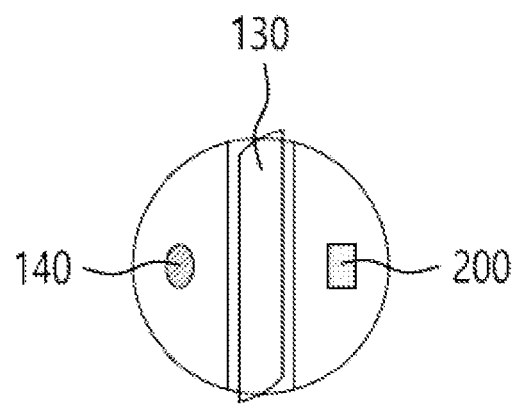
FIG. 2 is a schematic diagram showing a detail of FIG. 1.

FIG. 2 is a schematic diagram showing a detail of FIG. 1.

Referring to FIG. 1, the main module 100 may include a purifier 110, a transporter 120, a nozzle 130, and a light-emitter 140. The purifier 110 and the transporter 120 may be installed on one side of the space where the intelligent air shield formation device 1 is installed.

The nozzle 130 can control the direction in which purified air is discharged.

For this reason, the nozzle 130 may be opened or closed according to a control signal transmitted from the control module 300. Here, the opening of the nozzle 130 may mean a state in which purified air is discharged from the nozzle 130. When the nozzle 130 is closed, it may mean a state in which purified air is not discharged from the nozzle 130.

In addition, the nozzle 130 may control the direction in which purified air is discharged from the nozzle 130 according to a control signal transmitted from the control module 300.

The light-emitter 140 may be provided on one side of the nozzle 130, and the light-emitter 140 may emit light by the control module 300. In this case, the light-emitter 140 may be provided as an LED element or the like.

Figure 3:
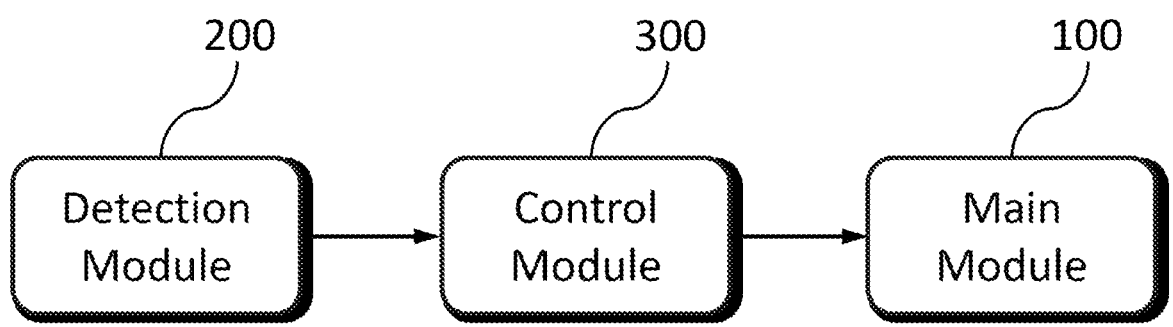
FIG. 3 is a block diagram showing the process of controlling the nozzle according to the body region in the control module of FIG. 1.

FIG. 3 is a block diagram showing the process of controlling the nozzle according to the body region in the control module of FIG. 1.

Referring to FIG. 3, the detection module 200 may detect a person using a space in which the main module 100 is provided. The detection module 200 may detect a detected human body region.

Also, the detection module 200 may detect noise generated from the body region side. The detection module 200 may generate noise information to indicate the level of noise. Also, the detection module 200 may measure the temperature of the body region to generate temperature information.

Accordingly, the control module 300 may generate region information of a shape surrounding the body region. The control module 300 may control a plurality of nozzles 130 corresponding to region information to discharge purified air.

Also, the control module 300 may generate movement information based on the speed at which the body region moves. The control module 300 may control the shape of the region information to be deformed based on the movement information.

Meanwhile, the control module 300 may control the area of the region information to increase as the temperature of the body region increases. In addition, the control module 300 may control the area of the region information to increase as the size of the noise information increases.

Through this, the nozzle 130 may be opened or closed according to a control signal transmitted from the control module 300. In addition, the nozzle 130 may control the direction in which purified air is discharged from the nozzle 130 according to a control signal transmitted from the control module 300.

Figure 4:
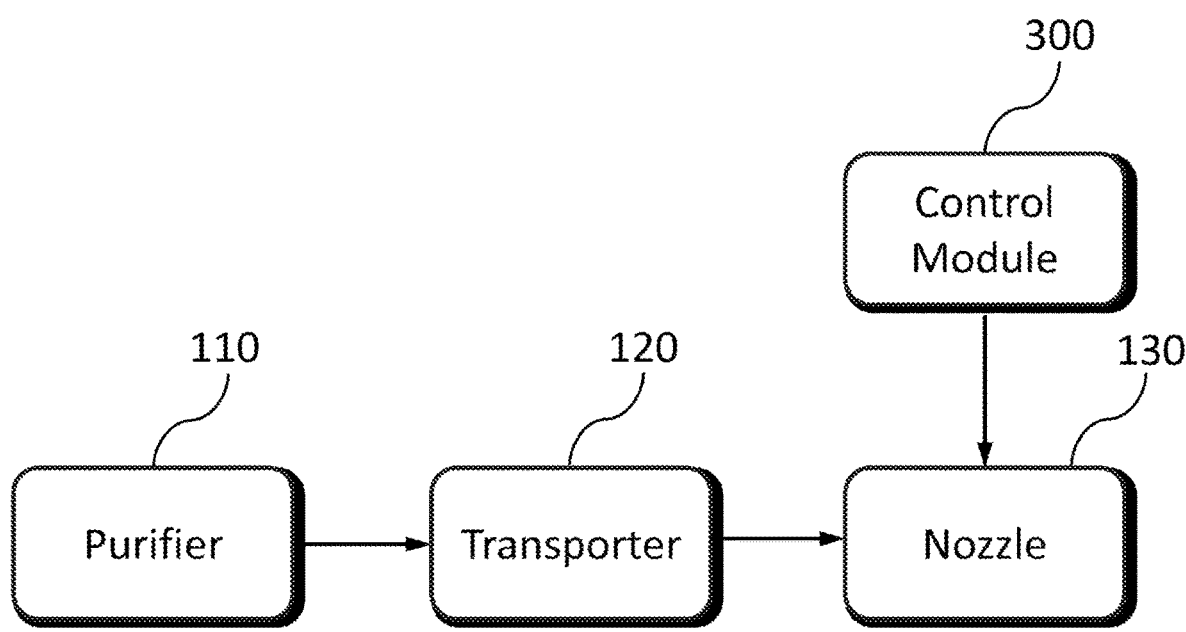
FIG. 4 is a block diagram showing the process of discharging purified air from the main module of FIG. 1.

FIG. 4 is a block diagram showing the process of discharging purified air from the main module of FIG. 1.

Referring to FIG. 4, the purifier 110 may induce air to be introduced, and the purifier 110 may purify the introduced air.

Accordingly, the transporter 120 may be provided to transport the purified air generated by the purifier 110. In addition, the transporter 120 may comprise one or more fans to allow purified air to be discharged to the outside of the nozzle 130 to form an air shield.

Here, the nozzle 130 may be provided to control the direction in which purified air is discharged.

For this reason, the nozzle 130 may be opened or closed according to a control signal transmitted from the control module 300. Here, the opening of the nozzle 130 may mean a state in which purified air is discharged from the nozzle 130. When the nozzle 130 is closed, it may mean a state in which purified air is not discharged from the nozzle 130. In addition, the nozzle 130 may control the direction in which purified air is discharged from the nozzle 130 according to a control signal transmitted from the control module 300.

FIGS. 5 to 8 are schematic diagrams illustrating an embodiment of extending region information in a control module.

Figure 5:
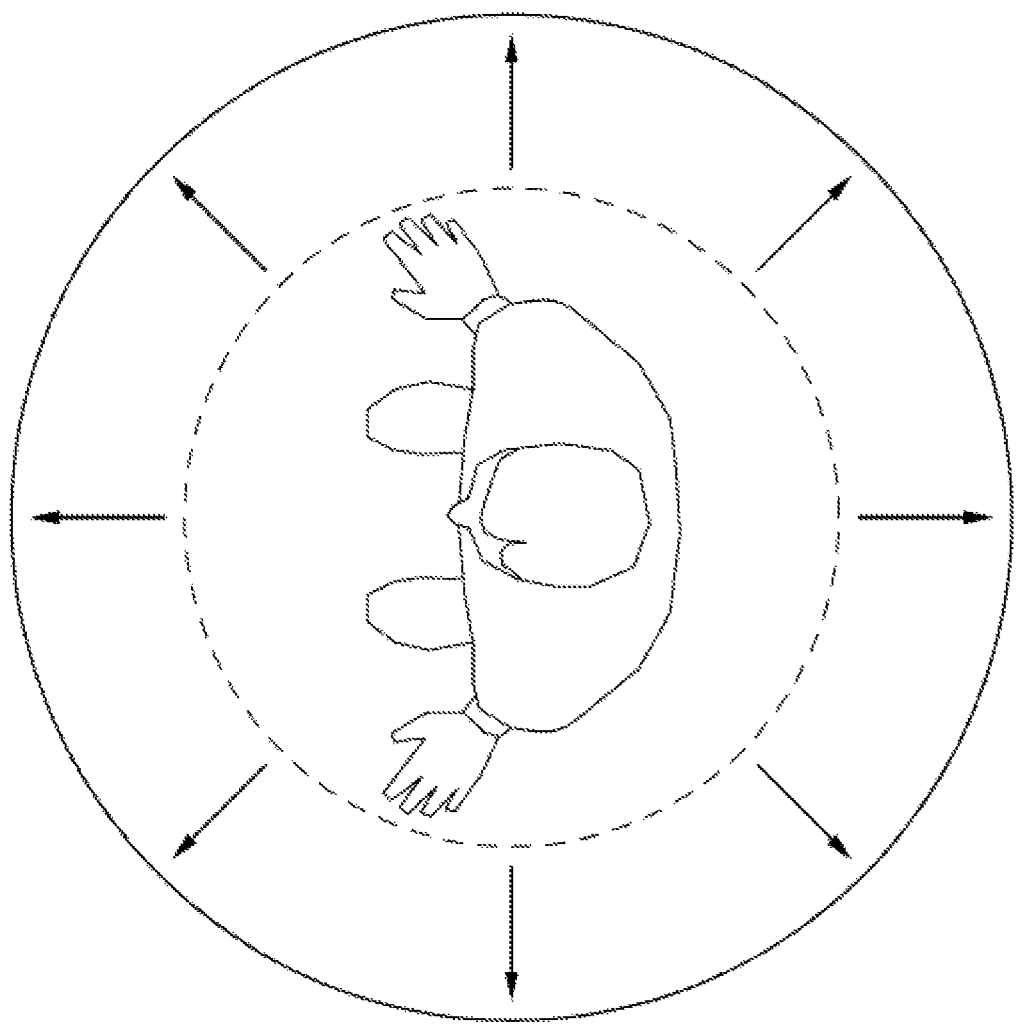
FIGS. 5 to 8 are schematic diagrams illustrating an embodiment of extending region information in a control module.

Referring to FIG. 5, it can be understood as a situation in which the area of region information is controlled to increase.

In this regard, the control module 300 may confirm that the area of the region information increases as the temperature of the body region increases.

In addition, the control module 300 may control the area of the region information to increase as the size of the noise information increases.

Figure 6:
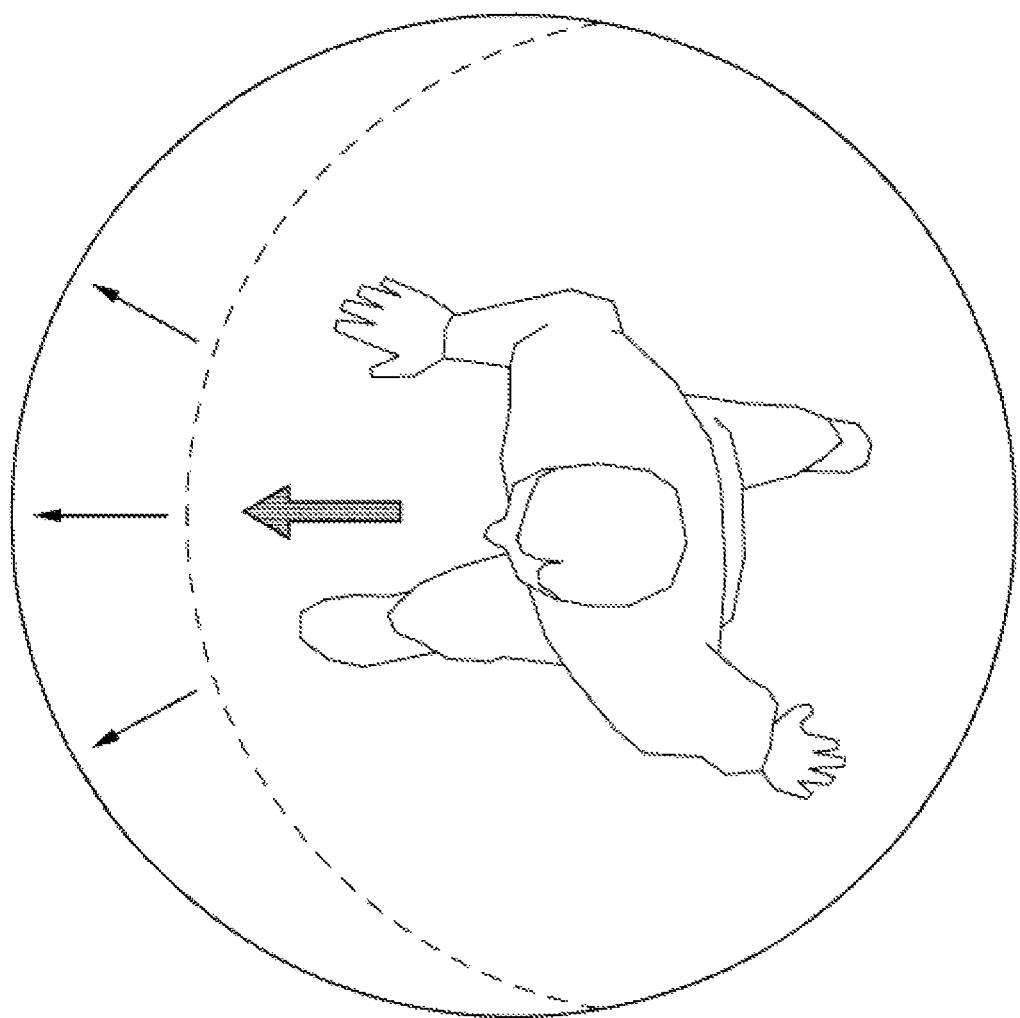

Referring to FIG. 6, it can be seen that the area in the direction in which a person moves is increased in the region information.

In this regard, the control module 300 may generate movement information based on the speed at which the body region moves, and the control module 300 may control the shape of the region information to be deformed based on the movement information.

In this case, as the speed according to the movement information increases, the control module 300 may control the outer side in the direction according to the movement information in the region information to be farther from the center of the region information.

Figure 7:
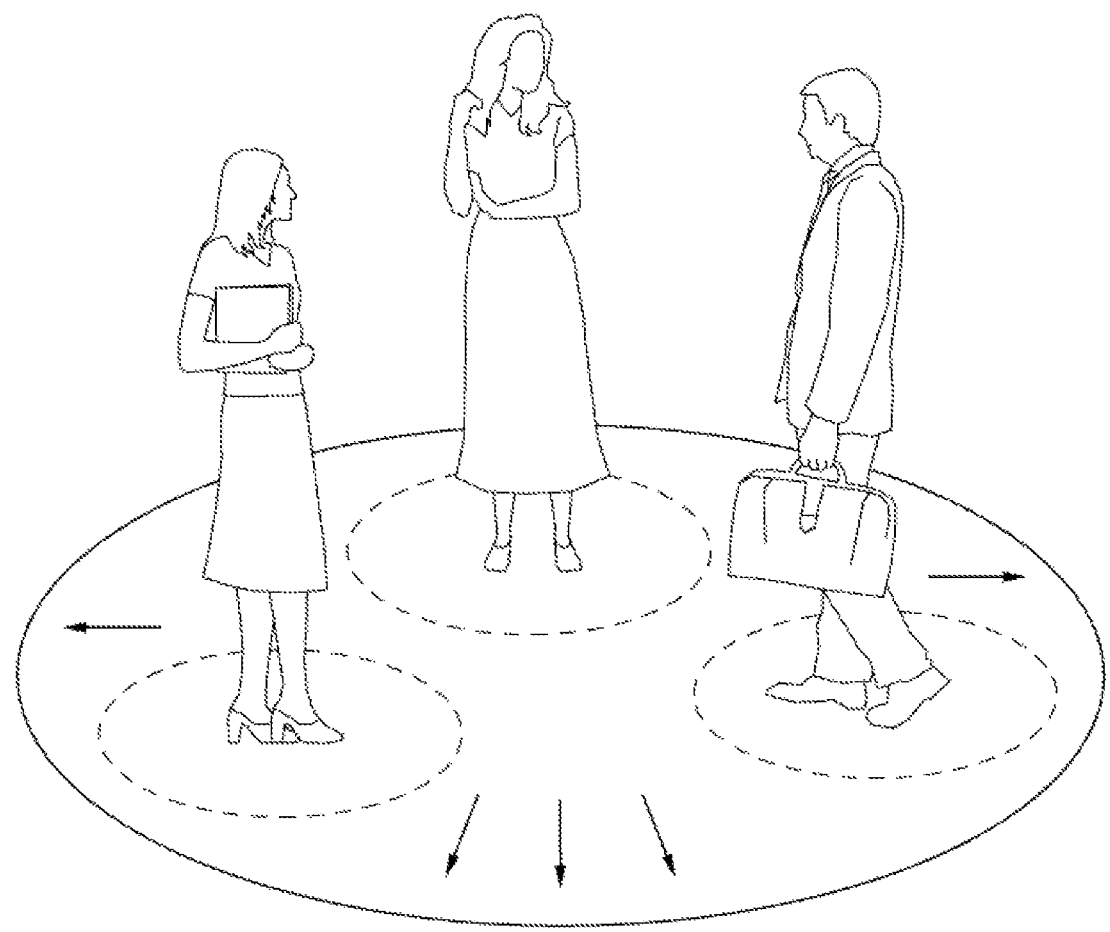
Figure 8:
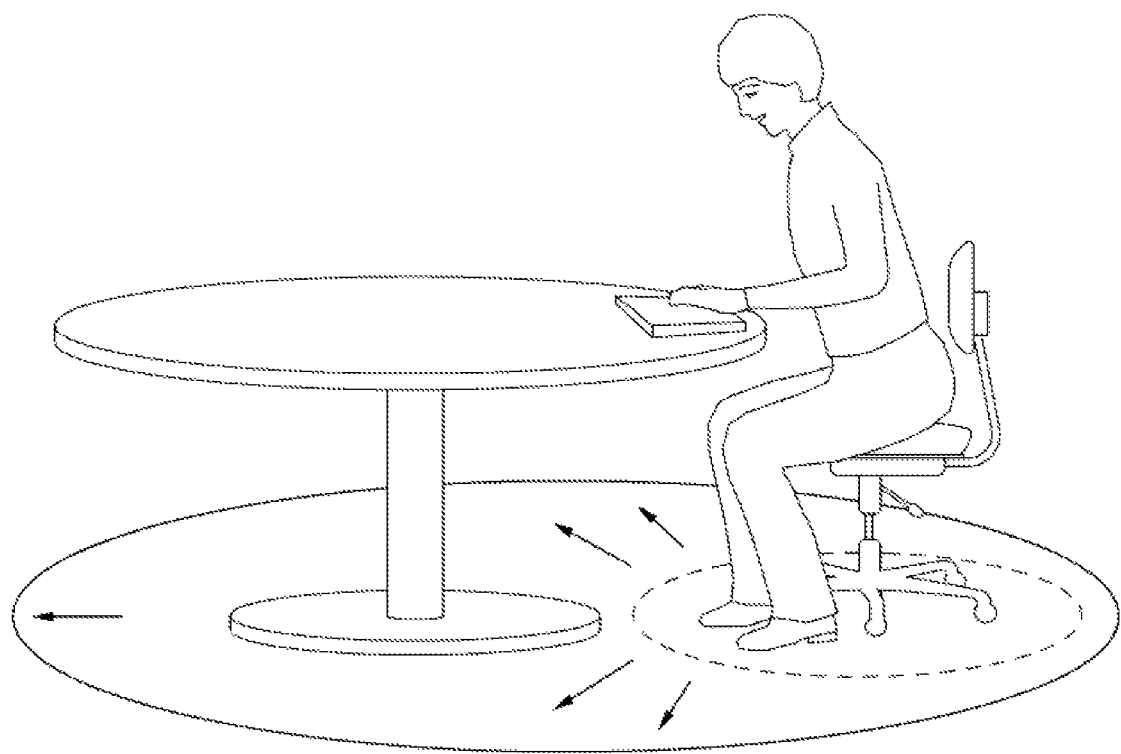

Referring to FIG. 7, region information extended to embrace a plurality of people may be identified.

In this regard, the control module 300 may control the nozzle 130 so that, when different people are adjacent to each other by a predetermined distance or more, the adjacent people are comprised inside one air shield.

For this reason, the control module 300 determines that the plurality of body regions converge to an arbitrary face-to-face region based on the plurality of movement information, and the outside of the direction according to the movement information in each region information When a distance interval from the face-to-face region is less than or equal to a preset first distance interval, each region information may be extended to one region information embracing a plurality of body regions.

Figure 9:
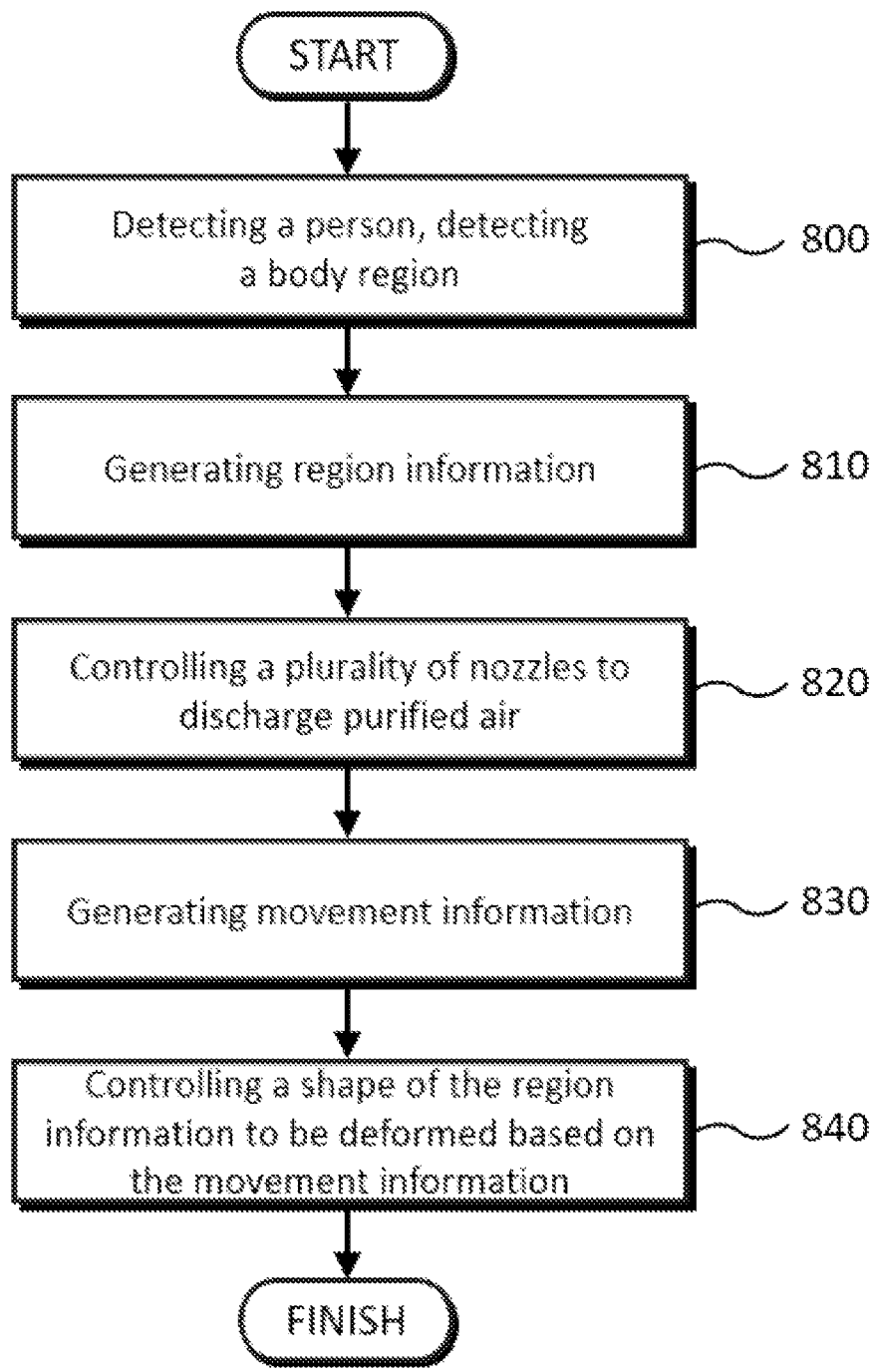
FIG. 9 is a flowchart of a method for forming an intelligent air shield according to an embodiment of the present invention.

FIG. 9 is a flowchart of a method for forming an intelligent air shield according to an embodiment of the present invention.

Since the intelligent air shield formation method according to an embodiment of the present invention proceeds on substantially the same configuration as the intelligent air shield formation device 1 shown in FIG. 1, the same reference numerals are assigned to the elements to same configuration as the intelligent air shield formation device 1 in FIG. 1, and repeated descriptions will be omitted.

The intelligent air shield formation method detects a person, detects the body region, (operation 800), generates region information (operation 810), controls the nozzle to discharge purified air (operation 820), generates movement information It may comprise an operation (operation 840) of controlling the shape of the region information to be deformed based on the operation (operation 830) and the movement information.

The operation 800 of detecting a person and detecting a body region may be an operation in which the detection module 200 detects a person using the space in which the main module 100 is provided and detects the body region of the detected person.

The operation 810 of generating the region information may be an operation in which the control module 300 generates region information having a shape surrounding the body region.

The operation 820 of controlling the nozzle to discharge purified air may be an operation in which the control module 300 controls a plurality of nozzles corresponding to region information to discharge purified air.

The operation 830 of generating movement information may be an operation in which the control module 300 generates movement information based on the speed at which the body region moves.

The operation 840 of controlling the shape of the region information to be deformed based on the movement information may be an operation of the control module 300 controlling the shape of the region information to be deformed based on the movement information.

According to one aspect of the present invention described above, by providing an intelligent air shield formation device and method capable of preventing infection, an air shield can be created around people so that infection among people can be prevented in a space where the intelligent air shield formation device is installed.

Although the above has been described with reference to the embodiments, those skilled in the art will understand that various modifications and changes can be made to the present invention without departing from the idea and scope of the present invention as set forth in the following claims.

What is claimed is:

1. An intelligent air shield formation device comprising:
a main module comprising a plurality of nozzles configured to discharge purified air;
a sensor configured to:
detect a person located at a space provided with the main module; and
detect a body region of the detected person; and
a control module configured to:
generate region information based on an area surrounding the body region;
control one or more of the plurality of nozzles corresponding to the region information to generate an air shield having a shape corresponding to the area surrounding the body region such that the detected person is located inside the air shield;
generate movement information based on a speed of movement of the body region caused by movement of the detected person; and
cause a size or the shape of the air shield to be changed or cause the air shield to move based on the movement information such that the moving person is continuously located inside the air shield,
wherein the air shield provided around the body region prevents the detected person from being infected or from infecting other people outside of the air shield at an indoor space, or the air shield minimizes the possibility of spreading droplets originated from the detected person.

2. The intelligent air shield formation device of claim 1, wherein the main module further comprises:
a purifier configured to induce air to be introduced, and purify the air;
a transporter configured to transport the purified air generated by the purifier; and
a light-emitter configured to emit light to sterilize the purified air,
wherein the control module is further configured to control directions of the plurality of nozzles such that the one or more nozzles corresponding generating the air shield direct the discharged sterilized air to the body region.

3. The intelligent air shield formation device of claim 1, wherein the sensor comprises a microphone and is further configured to detect a noise generated from the body region, and generate noise information to indicate a level of the noise, and
wherein the control module is further configured to cause the size of the air shield to be increased based on the noise information as the level of the noise increases.

4. The intelligent air shield formation device of claim 3, wherein, in case that at least part of an extended region information based on the level of the noise overlaps at least part of an other region information, the control module is further configured to:
recognize an overlapping region in which the extended region information and the other region information overlaps,
calculate an angle of at least one nozzle among the plurality of nozzles corresponding to the overlapping region,
cause the at least one nozzle corresponding to the overlapping region to be inclined to inside of the other region according to the angle of the at least one nozzle.

5. The intelligent air shield formation device of claim 1, wherein the control module is further configured to:
indicate a location at which an arbitrary object is installed,
set an object region including the location at which the object is installed,
recognize an overlapping region where the region information and the location at which the object is installed overlaps, and
extend the object region by including the region information to the object region, when an area of the overlapping region is greater than or equal to a predetermined area of the object.

6. The intelligent air shield formation device of claim 1, wherein:
the sensor is further configured to detect a plurality of persons at the space; and
the control module is further configured to cause the size of the air shield to be adjusted based on a size of an area surrounding a plurality of regions of the detected plurality of persons such that the size of the air shield is increased as a number of the detected plurality of persons increases.

7. The intelligent air shield formation device of claim 1, wherein the control module is further configured to cause a different one of the plurality of nozzles to discharge the purified air when the detected person moves from one area surrounding the body region to another area to maintain the air shield around the detected person.

8. The intelligent air shield formation device of claim 1, wherein:
the sensor is further configured to detect a plurality of persons at the space; and
the control module is further configured to control the one or more nozzles such that a first person among the detected plurality of persons and a second person among the detected plurality of persons are located inside a same air shield based on a distance between the first person and the second person.

9. The intelligent air shield formation device of claim 1, wherein:
the sensor is further configured to detect a plurality of persons at the space; and
the control module is further configured to generate a plurality of air shields such that a first air shield of the plurality of air shields has a shape corresponding to an area surrounding at least a first person among the detected plurality of persons and a second air shield of the plurality of air shields has a shape corresponding to an area surrounding at least a second person among the detected plurality of persons.

10. The intelligent air shield formation device of claim 1, wherein the plurality of nozzles is located on a top side of the main module such that the purified air is discharged downwards from the top side towards ground, and the shape of the air shield is a circular shape.

11. The intelligent air shield formation device of claim 1, wherein:
the main module further comprises a light-emitter located next to each of the plurality of nozzles;
the light-emitter is turned on when a corresponding one of the plurality of nozzles discharging the purified air is open;
the light-emitter is turned off when a corresponding one of the plurality nozzles is closed and not discharging the purified air; and
the light-emitter is configured to emit light to sterilize the purified air being discharged.

12. The intelligent air shield formation device of claim 1, wherein:
the sensor comprises at least one of a thermal camera or a thermal sensor, and configured to generate temperature information by measuring a temperature of the body region; and
the control module is further configured to cause a size of the air shield to be increased based on the temperature information as the temperature of the body region increases such that the size or shape of the air shield is adjusted according to the measured temperature.

13. The intelligent air shield formation device of claim 1, wherein the one or more of the plurality of nozzles discharging the purified air are open while other nozzles among the plurality nozzles not discharging the purified air are closed.

14. The intelligent air shield formation device of claim 13, wherein the control module is further configured to transmit a control signal to the one or more of the plurality of nozzles such that a direction of the discharging the purified air is changed according to the control signal.

15. The intelligent air shield formation device of claim 14, wherein the control module is further configured to transmit a first control signal to the one or more of the plurality of nozzles such that the purified air is discharged vertically from a top side of the main module towards ground according to the first control signal.

16. The intelligent air shield formation device of claim 15, wherein the control module is further configured to transmit a second control signal to the one or more of the plurality of nozzles such that the purified air is discharged in an inclined direction compared to the vertical discharging according to the second control signal.

* * * * *